US008304421B2

(12) United States Patent
Crooks et al.

(10) Patent No.: US 8,304,421 B2
(45) Date of Patent: Nov. 6, 2012

(54) INDOLE COMPOUNDS AND THEIR USE AS RADIATION SENSITIZING AGENTS AND CHEMOTHERAPEUTIC AGENTS

(75) Inventors: Peter A. Crooks, Nicholasville, KY (US); Thirupathi R. Yerramreddy, Lexington, KY (US); Narsimha R. Penthala, Lexington, KY (US); Michael L. Freeman, Franklin, TN (US); Sekhar R. Konjeti, Nashville, TN (US)

(73) Assignees: Vanderbilt University, Nashville, TN (US); University of Kentucky Research Foundation, Lexington, KY (US)

( * ) Notice: Subject to any disclaimer, the term of this patent is extended or adjusted under 35 U.S.C. 154(b) by 411 days.

(21) Appl. No.: 12/571,425

(22) Filed: Sep. 30, 2009

(65) Prior Publication Data
US 2010/0081678 A1 Apr. 1, 2010

Related U.S. Application Data

(60) Provisional application No. 61/194,754, filed on Sep. 30, 2008.

(51) Int. Cl.
*A61K 31/515* (2006.01)
*A61K 31/415* (2006.01)
*C07D 401/06* (2006.01)
*C07D 233/02* (2006.01)

(52) U.S. Cl. ...... 514/270; 514/385; 544/300; 548/311.4
(58) Field of Classification Search .................. 514/270, 514/385; 544/300; 548/311.4
See application file for complete search history.

(56) References Cited

U.S. PATENT DOCUMENTS

| | | | |
|---|---|---|---|
| 5,057,614 A | 10/1991 | Davis et al. | |
| 5,405,864 A | 4/1995 | Broka | |
| 5,696,148 A | 12/1997 | Lundbech et al. | |
| 6,753,379 B1 | 6/2004 | Kawate et al. | |
| 6,753,394 B2 | 6/2004 | Weikard et al. | |
| 6,756,394 B1 | 6/2004 | Yuan et al. | |
| 6,939,873 B2 | 9/2005 | Gutman et al. | |
| 7,491,743 B2 | 2/2009 | Cuny et al. | |
| 2003/0105119 A1 | 6/2003 | Bazin et al. | |
| 2003/0153589 A1 | 8/2003 | Moros et al. | |
| 2003/0187005 A1 | 10/2003 | Gutman et al. | |
| 2003/0229108 A1 | 12/2003 | DeBelin et al. | |
| 2004/0214845 A1 | 10/2004 | Bazin et al. | |
| 2004/0266843 A1 | 12/2004 | Howlett et al. | |
| 2005/0119260 A1 | 6/2005 | Cuny et al. | |
| 2006/0035915 A1 | 2/2006 | Gutman et al. | |
| 2008/0113993 A1 | 5/2008 | DeBelin et al. | |

FOREIGN PATENT DOCUMENTS
WO WO2007/062399 5/2007

OTHER PUBLICATIONS

Bradbury, C. M., Markovina, S., Wei, S. J., Rene, L. M., Zoberi, I., Horikoshi, N. and Gius, D. (2001) Indomethacin-induced radiosensitization and inhibition of ionizing radiation-induced NF-KB activation in HeLa cells occur via a mechanism involving p38 MAP kinase. Cancer Res, vol. 61, pp. 7689-7696.

Geng, Ling Indolyl-quinuclidinols inhibit ENOX activity and endothelial cell morphogenesis while enhancing radiation-mediated control of tumor vasculature, The FASEB Journal, vol. 23, Sep. 2009, pp. 2986-2995.

Kampinga, H. H. and Dikomey, E. (2001) Hyperthermic radiosensitization: mode of action and clinical relevance. Int J Radiat Biol 2001, vol. 77, pp. 399-408.

Kim KW, Mutter RW, Cao C, Albert JM, Shinohara ET, Sekhar KR, Lu B. (2006) Inhibition of signal transducer and activator of transcription 3 activity results in down-regulation of Survivin following irradiation. Mol Cancer Ther. 5:2659-2665.

Locke, J. E., Bradbury, C. M., Wei, S. J., Shah, S., Rene, L. M., Clemens, R. A., Roti Roti, J., Horikoshi, N. and Gius, D. (2002) Indomethacin lowers the threshold thermal exposure for hyperthermic radiosensitization and heat-shock inhibition of ionizing radiation-induced activation of NF-kB. Int J Radiat Biol, 78, 493-502.

Nielsen, O. S., Horsman, M. and Overgaard, J. (2001) A future for hyperthermia in cancer treatment? Eur J Cancer, 37, 1587-1589.

Okunieff, Paul et al., Report from the Radiation Therapy Committee of the Southwest Oncology Group (SWOG): Research Objectives Workshop 2008, Clin Cancer Res 2009; 15(18) Sep. 15, 2009, pp. 5663-5670.

Raaphorst, G. P. and Azzam, E. I. (1983) Thermal radiosensitization in Chinese hamster (V79) and mouse C3H 10T ½ cells. The thermotolerance effect. Br J Cancer, 48, 45-54.

Reddy, Y. Thirupathi et al., Novel substituted (Z)-5-((N-benzyl-1H-indol-3-yl)methylene)imidazolidine-2,4-diones and 5-((N-benzyl-1H-indol-3-yl)methylene)pyrimidine-2,4,6(1H,3H,5H)-triones as potent radio-sensitizing agents, (2010).

Sekhar KR, Sonar VN, Muthusamy V, Sasi S, Laszlo A, Sawani J, Horikoshi N, Higashikubo R, Bristow RG, Borrelli MJ, Crooks PA, Lepock JR, Roti Roti JL, Freeman ML. (2007). Novel chemical enhancers of heat shock increase thermal radiosensitization through a mitotic catastrophe pathway. Cancer Res, vol. 67: 695-701.

Sekhar, KR et al. (2002) Redox-Sensitive Interaction Between KIAA0132 and Nrf2 Mediates Indomethacin-Induced Expression of γ-Glutamylcysteine Synthetase, Free Radical Biology & Medicine, vol. 32, No. 7, pp. 650-662.

Sekhar, KR et al. (2003) NADPH Oxidase Activity is Essential for Keap1/Nrf2-mediated Induction of GCLC in Response to 2-Indol-3-yl-methylenequinuclidin-3-ols1, Cancer Research vol. 63, 5636-5645.

Senisterra, G et al., Destabilization of the Ca2+-ATPase of Sarcoplasmic Reticulum by Thiol-Specific, Heat Shock Inducers Results in Thermal Denaturation at 37° C, Biochemistry 1997, vol. 36, pp. 11002-11011.

Sonar VN, Thirupathi Reddy Y, Sekhar KR, Sasi S, Freeman ML, Crooks PA, Novel substituted (Z)-2-(N-benzylindol-3-ylmethylene)-quinuclidin-3-one and (Z)-(+/−)-2-(N-benzylindol-3-ylmethylene)-quinuclidin-3-ol derivatives as potent thermal sensitizing agents Bioorganic & Medicinal Chemistry Letters 17 (2007) pp. 6821-6824.

Wynstra, J. H., Wright, W. D., Higashikubo, R. and Roti Roti J. L. (1990) Repair of radiation-induced DNA damage in thermotolerant and nonthermotolerant HeLa cells. Radiat Res, 124, 85-89.

(Continued)

*Primary Examiner* — James O Wilson
*Assistant Examiner* — Ebenezer O Sackey
(74) *Attorney, Agent, or Firm* — Stites & Harbison PLLC; Richard S. Myers, Jr.

(57) ABSTRACT

Indole derivatives that are useful in the treatment of cancer as a chemotherapeutic agent or radiosensitizing agent.

14 Claims, 6 Drawing Sheets

OTHER PUBLICATIONS

Xu, M., Myerson, R. J., Straube, W. L., Moros, E.G., Lagroye, I., Wang, L. L., Lee, J. T.and Roti Roti, J. L. (2002) Radiosensitization of heat resistant human tumor cells by 1 hour at 41.1° C and its effect on DNA repair. Int J Hyperthermia, vol. 18, No. 5m pp. 385-403.

Zhou-Guang, H., Yexiong, L., Weizhi, Y., Junxin, W. and Zihao, Y. (2003) Abrogation of radiation-induced G2 arrest and radiosensitization by 7-hydroxystaurosporine (UCN-01) in human nasopharyngeal carcinoma cell line. Chines Journal of Cancer, 2003, vol. 22(1), pp. 6-10.

FACS analysis of γH2AX – 4 Gy

INDOLE COMPOUNDS AND THEIR USE AS RADIATION SENSITIZING AGENTS AND CHEMOTHERAPEUTIC AGENTS

PRIOR APPLICATIONS

This invention claims benefit to U.S. Patent Application No. 61/194,754, filed Sep. 30, 2008, the contents of which is incorporated herein in its entirety.

FIELD OF THE INVENTION

Generally, the present invention relates to the field of radiation sensitizers. Additionally, the present invention relates to the field of chemotherapeutic agents.

One aspect of the present invention relates to novel indole compounds. Another aspect of the present invention relates to the use of indole compounds as radiation sensitizers.

Another aspect of the present invention relates to the use of indole compounds as chemotherapeutic agents.

Another aspect of the present invention is 5-((N-benzyl-1H-indol-3-yl)methylene)pyrimidine-2,4,6(1H,3H,5H)-triones & (Z)-5-((N-benzyl-1H-indol-3-yl)methylene)imidazolidine-2,4-diones and analogs thereof. Another aspect of the present invention is the use of 5-((N-benzyl-1H-indol-3-yl)methylene)pyrimidine-2,4,6(1H,3H,5H)-triones & (Z)-5-((N-benzyl-1H-indol-3-yl)methylene)imidazolidine-2,4-diones and analogs thereof as radiation sensitizers.

Another aspect of the present invention is 4-((3-((2,4,6-Trioxotetrahydropyrimidin-5(6H)-ylidene)methyl)-1H-indol-1-yl)methyl)benzo-nitrile, and Methyl-4-((3-((2,4,6-trioxotetrahydro pyrimidin-5(6H)-ylidene)methyl)-1H-indol-1-yl)methyl)benzoate, and uses thereof, including the uses described herein.

These and other aspects and uses would be evident to one of ordinary skill in the art.

BACKGROUND OF THE INVENTION

Radiotherapy is the treatment of cancer and other diseases with ionizing radiation. Radiotherapy is used in curative therapy, palliative therapy, adjuvant therapy after or before surgery, simultaneous radio-chemotherapy, etc. Radiotherapy is successful because ionizing radiation kills dividing cells and is thus slightly more toxic to fast growing cancer cells. Radiotherapy may be used to treat localized solid tumors, such as cancers of the skin, tongue, larynx, brain, breast, or uterine cervix. Agents which are used to potentiate the effectiveness of radiation therapy in destroying unwanted cells are radiation sensitizing agents. Various attempts have been made to develop a radiation sensitizer that reduces the radiation dose and adverse drug reactions without compromising the therapeutic effect of radiotherapy.

For example, 7-Hydroxystaurosporine (UCN-01) is used as a radiosensitizing agent (Zhouguang et al., 2003) in radiotherapy to increase the radiosensitivity of tumor cells. The sulfonamide-substituted indolinones have been invented as radiation sensitizing agents (Anthony et al., U.S. Pat. Appl. Publ. 2004, 46 pp), which are capable of enhancing radiotherapy by inhibiting DNA-protein kinase (DNA-PK).

Radiotherapy is often performed for various types of cancers such as gastric cancer, colorectal cancer, pancreatic cancer, head and neck cancer, esophageal cancer, lung cancer, and breast cancer that are advanced to stage III or IV.

Radiation therapy combined with adjuvant hyperthermia has the potential to provide outstanding local-regional control for refractory disease. Hyperthermia is an extremely effective radiation sensitizer, yielding thermal enhancement factors of up to 5.0 (Kampinga and Dikomey, 2001; Raaphorst and Azzam, 1983). However, hyperthermia is limited clinically as a result of the technical problems of heat delivery (Nielsen et al., 2001). Hence there is an urgent need to develop pharmacological agents that can be used to replace hyperthermia. Previous work has established that indomethacin can act as a radiation sensitizer (Bradbury et al., 2001; Locke et al., 2002) and enhancer of thermal radiosensitization, and also it has been shown from other independent work that indomethacin lowers the temperature necessary for the heat-induced protein aggregation and lowers the temperature necessary for Hsf-1 activation, such that a complete heat shock response can be attained at temperatures that are by themselves, insufficient for activation. Although indomethacin is used as a radiation sensitizer in radiotherapy, it is highly toxic at high concentrations. Hence there is a need to invent pharmacological agents with lower toxicity.

The present inventors previously discovered novel indole as potent thermal radiosensitizers capable of lowering the threshold for Hsf1 activation and thermal sensitivity. Additionally, the present inventors previously discovered (Z)-2-(N-benzylindol-3-ylmethylidene)quinuclidin-3-ol and Z-(±)-2-[N-(4-chlorobenzyl)indole-3-ylmethylidene]quinuclidin-3-ol as potent thermal radiosensitizers capable of lowering the threshold for Hsf1 activation and thermal sensitivity (Sekhar et al. 2007; Sonar et al. 2007). These compounds needed 41° C. temperature to produce radiosensitization. It is difficult to achieve such temperatures in tumors. In order to lower the temperatures, the above compounds were modified and tested for their ability to induce heat shock effect and finally radiosensitization.

The indole derived Aplysinopsin analogs have been reported as potent and selective cytotoxic agents against cancer cells. These observations prompted us to design and synthesize a series of novel indole derivatives, including substituted 5((N-Benzyl-1H-indol-3-yl)methylene)pyrimidine-2,4,6(1H,3H,5H)-triones & (Z)-5((N-benzyl-1H-indol-3-yl)methylene)imidazolidine-2,4-diones and their related compounds with various substitutions on both the indolic ring and the N-benzyl group that are radiation sensitizers by eliminating the necessity of heat.

SUMMARY AND ASPECTS OF THE PRESENT INVENTION

The present invention comprises novel structural entities have been designed and synthesized that constitute a series of novel functionalized indole analogs and other molecules structurally related to indomethacin in order to maximize radiosensitization activity and minimize toxicity.

Another object of the present invention is to provide a radiotherapy enhancer that can reduce the radiation dose and adverse drug reactions when used in combination with cancer radiotherapy.

One embodiment of the present invention is a series of novel substituted N-benzyl aplysinopsin analogs were synthesized by aldol condensation of the appropriate substituted N-benzyl indole-3-carboxaldehyde with a selection of active methylene compounds like barbituric acid & its related compounds, hydantoin & its related compounds. The structure and purity of these derivatives was verified by $^1$H and $^{13}$C-NMR spectroscopy.

As a result, novel substituted 5((N-Benzyl-1H-indol-3-yl)methylene)pyrimidine-2,4,6(1H,3H,5H)-triones & (Z)-5-((N-benzyl-1H-indol-3-yl)methylene)imidazo-lidine-2,4-diones and their related compounds were synthesized and evaluated for their radiosensitization properties against HT-29 cells. Also, embodiments were tested against tubule formation by HUVECs to assess their potency to inhibit angiogenesis. As an example, Compound 1 inhibited the tubule formation by HUVECs, shown below.

An additional aspect of the present invention is a cancer treatment method provided by using a composition of the present invention and radiation in combination. Tumors for which this treatment method can be used are not particularly limited. This method is particularly suitable for cancers with high radiation sensitivity. However, since the radiation enhancer of the present invention can also increase radiation sensitivity of cancers that are considered to have low sensitivity, improvement of the effect of cancer radiotherapy can be expected. Examples of such cancers include head and neck cancer, esophageal cancer, gastric cancer, colorectal cancer, liver cancer, gallbladder/bile duct cancer, pancreatic cancer, lung cancer, breast cancer, bladder cancer, prostate cancer, cervical cancer, brain tumor, malignant lymphoma, acute leukemia, chronic leukemia, medulloblastoma, retina retinoblastoma, neuroblastoma, Wilms' tumor, Hodgkin's disease, multiple myeloma, plasmacytoma, thymoma, basal cell cancer, squamous cancer, Ewing's tumor, thyroid cancer, ovary cancer, salivary gland cancer, teratoma, malignant melanoma, neuroglioma, renal cell carcinoma, osteosarcoma, and so forth.

BRIEF DESCRIPTION OF THE DRAWINGS

The figures are presented as being exemplary of the present invention, and are not to be construed as being limiting thereof. In general, the figures show experimental data that provide evidence of the radiation sensitization properties of the indole analogs described herein.

FIG. 1 is a chart that shows the results of test in connection with Compound 1. More specifically, Compound 1 was tested on HT-29 cells for colony formation assay. Various concentrations of Compound 1 was used to assess the potency of the compound in exerting radiation sensitization property. HT-29 cells were treated with Compound 1 for 30 min and various doses of radiation was applied. The cells were incubated for 90 min more. The cells were washed with PBS and fresh medium was added. Colonies that were formed after 2 weeks of incubation, were counted and corrected for drug toxicity and expressed as survival fraction.

FIG. 2: HT-29 cells were treated with Compound 1 for 2 hrs. The drug was washed off with PBS and fresh medium was added. The cells were incubated for 5 more hours and nuclear protein was extracted and Gel Mobility Shift Assay was performed as described in Experimental section, below.

DETAILED DESCRIPTION OF THE INVENTION

The present invention can be understood more readily by reference to the following detailed description of the invention and the Examples included therein.

Before the present compounds, compositions, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which need to be independently confirmed.

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "optional" or "optionally" means that the subsequently described event or circumstance can or can not occur, and that the description includes instances where said event or circumstance occurs and instances where it does not.

As used herein, the term "subject" refers to a target of administration. The subject of the herein disclosed methods can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. A patient refers to a subject afflicted with a disease or disorder. The term "patient" includes human and veterinary subjects.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "radiation sensitizer" can be construed as an agent that enhances the anti-tumor effect more than irradiation alone by using the sensitizer in combination with irradiation.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, the term "effective amount" refers to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side affects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

Additionally, when used in reference to compounds of the invention, "an effective amount" refers to doses of compound sufficient to provide circulating concentrations high enough to impart a beneficial effect on the recipient thereof for at least either treating tumors or cancers, or enhancing radiation therapy. The precise amount to be administered can be determined by the skilled practitioner in view of desired dosages, side effects and medical history of the patient.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

Additionally, Examples of pharmaceutically acceptable salts include alkaline or alkaline earth metal ion salts, particularly $Na^+$ or $K^+$ salts, or similar pharmaceutically-acceptable inorganic salts. The above salt forms in all polymorphic and amorphous forms, may be in some cases hydrates or solvates with alcohols and other solvents.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, optionally substituted alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, optionally substituted alkyl, cycloalkyl, alkoxy, amino, ether, halide, hydroxy, nitro, silyl, sulfo-oxo, or thiol as described herein.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "alkylaryl" refers to alkyl-substituted aryl groups and "substituted alkylaryl" refers to alkylaryl groups further bearing one or more substituents as set forth above.

The term "arylalkyl" refers to aryl-substituted alkyl groups and "substituted arylalkyl" refers to arylalkyl groups further bearing one or more substituents as set forth above.

The term "arylalkenyl" refers to aryl-substituted alkenyl groups and "substituted arylalkenyl" refers to arylalkenyl groups further bearing one or more substituents as set forth above.

The term "arylalkynyl" refers to aryl-substituted alkynyl groups and "substituted arylalkynyl" refers to arylalkynyl groups further bearing one or more substituents as set forth above.

The term "aroyl" refers to aryl-substituted species such as benzoyl and "substituted aroyl" refers to aroyl moieties further bearing one or more substituents as set forth above.

The term "heteroaryl" refers to cyclic moieties containing one or more heteroatoms as part of the ring structure, and having in the range of 3 up to 12 carbon atoms and "substituted heteroaryl" refers to heterocyclic moieties further bearing one or more substituents as set forth above.

The term "acyl" refers to alkyl-carbonyl species.

The term "halogen" refers to fluoride, chloride, bromide or iodide atoms.

As indicated above, an aspect of the present invention is the treatment of cancers including, for example, lung carcinomas, breast cancers, prostate cancers, cancers of the cervix and endometrium, neuroblastomas, lymphomas, gliomas, melanomas, squamous cell carcinomas, sarcomas, adenocarcinomas, astrocytomas, head-and-neck tumors, and GI tumors.

One embodiment of the present invention is compounds of the following formulae:

Structure 1

Structure 2 and isomers, i.e. enantiomers, diastereomers, and geometrical isomers thereof.

In the above structures, where the two dotted bonds in Structure 1 & Structure 2 can be either single bonds or double bonds, or a combination of both. When a double bond is present in Structure 2, the two possible E and Z forms are included.

In the above formulas, X is chosen from O or N. Where R is hydrogen atom; methyl group; phenyl or substituted phenyl group. $R^1, R^2, R^3, R^4, R^5, R^6, R^7, R^8, R^9, R^{10}$ and $R^{11}$ are each independently selected from hydrogen; alkyl; substituted alkyl; cycloalkyl; substituted cycloalkyl, alkenyl; substituted alkenyl; alkynyl; substituted alkynyl; aryl; substituted aryl; alkylaryl; substituted alkylaryl; arylalkyl; substituted arylalkyl; arylalkenyl; substituted arylalkenyl; arylalkynyl; substituted arylalkynyl; arylalkenyl; substituted arylalkenyl; arylalkynyl; substituted arylalkynyl; heteroaryl; substituted heteroaryl; trifluoromethyl; halogen; cyano; nitro; amidinea; amino; carboxyl; ester; alkylalkylamino; dialkylamino; hydroxyl; alkoxy or arylalkoxy (e.g. methoxy, ethoxy, benzyloxy, substituted benzyloxy).

A pharmaceutical composition containing a compound of the invention is also contemplated, which may include a conventional additive, such as a stabilizer, buffer, salt, preservative, filler, flavor enhancer and the like, as known to those skilled in the art. Representative buffers include phosphates, carbonates, citrates and the like. Exemplary preservatives include EDTA, EGTA, BHA, BHT and the like. A composition of the invention may be administered orally, i.e., in solid or liquid form (tablet, gel cap, time release capsule, powder, solution, or suspension in aqueous or non aqueous liquid; intravenously as an infusion or injection, i.e., as a solution, suspension or emulsion in a pharmaceutically acceptable carrier.

Examples of the present invention specific include the following compounds:

| 1. R = CN | R1 = H |
| 2. R = COOCH₃ | R1 = H |
| 3. R = H | R1 = H |
| 4. R = NO₂ | R1 = H |
| 5. R = H | R1 = Cl |
| 6. R = H | R1 = OCH₃ |

| 7. R = CN | $R_1$ = H | $R_2$ = H |
| 8. R = H | $R_1$ = H | $R_2$ = H |
| 9. R = NO₂ | $R_1$ = H | $R_2$ = H |
| 10. R = Cl | $R_1$ = H | $R_2$ = H |
| 11. R = COOCH3 | $R_1$ = H | $R_2$ = H |
| 12. R = H | $R_1$ = Br | $R_2$ = H |
| 13. R = F | $R_1$ = H | $R_2$ = H |
| 14. R = H | $R_1$ = H | $R_2$ = Cl |
| 15. R = OCH₃ | $R_1$ = H | $R_2$ = Br |
| 16. R = H | $R_1$ = H | $R_2$ = CH₃ |
| 17. R = H | $R_1$ = H | $R_2$ = Br |
| 18. R = H | $R_1$ = H | $R_2$ = OCH₃ |
| 19. R = CH₃ | $R_1$ = H | $R_2$ = H |

Another embodiment of the present invention is the use of compounds disclosed herein in connection with at least one known anti-cancer treatment.

Thus, embodiments of the present invention relates to a method of treating cancer in a subject in need thereof, by administering to a subject in need thereof a first amount of a compound of the present invention or a pharmaceutically acceptable salt or hydrate thereof, in a first treatment procedure, and a second amount of an anti-cancer agent in a second treatment procedure, wherein the first and second amounts together comprise a therapeutically effective amount.

As discussed herein, treatment of cancer, as used herein, refers to partially or totally inhibiting, delaying or preventing the progression of cancer including cancer metastasis; inhibiting, delaying or preventing the recurrence of cancer including cancer metastasis; or preventing the onset or development of cancer (chemoprevention) in a mammal, for example a human.

As discussed above, the methods of the present invention are useful in the treatment in a wide variety of cancers, including but not limited to solid tumors, hematological malignancies, carcinomas, neuroblastoma, or melanoma.

The invention further relates to pharmaceutical combinations useful for the treatment of cancer. The pharmaceutical combination comprises a first amount of a compound of the present invention, e.g., compound 1, and a second amount of an anti-cancer agent. The first and second amount together comprise a therapeutically effective amount.

The invention further relates to the use of a first amount of a compound of the present invention and a second amount of an anti-cancer agent for the manufacture of a medicament for treating cancer.

In particular embodiments of this invention, the combination of the compound of the present invention and anti-cancer agent is additive, i.e. the combination treatment regimen produces a result that is the additive effect of each constituent when it is administered alone. In accordance with this embodiment, the amount of a compound of the present invention and the amount of the anti-cancer together constitute an effective amount to treat cancer.

In another particular embodiment of this invention, the combination of a compound of the present invention and anti-cancer agent is considered therapeutically synergistic when the combination treatment regimen produces a significantly better anticancer result (e.g., cell growth arrest, apoptosis, induction of differentiation, cell death) than the additive effects of each constituent when it is administered alone at a therapeutic dose. Standard statistical analysis can be employed to determine when the results are significantly better. For example, a Mann-Whitney Test or some other generally accepted statistical analysis can be employed.

The treatment procedures can take place sequentially in any order, simultaneously or a combination thereof. For example, the first treatment procedure, administration of a compound of the present invention, can take place prior to the second treatment procedure, i.e. the anti-cancer agent, after the second treatment with the anticancer agent, at the same time as the second treatment with the anticancer agent, or a combination thereof. For example, a total treatment period can be decided for a compound of the present invention inhibitor. The anti-cancer agent can be administered prior to onset of treatment with the compound of the present invention or following treatment with the compound of the present invention. In addition, treatment with the anti-cancer agent can be administered during the period of compound of the present invention administration but does not need to occur over the entire compound of the present invention treatment period. Similarly, treatment with the compound of the present invention can be administered during the period of anti-cancer agent administration but does not need to occur over the entire anti-cancer agent treatment period. In another embodiment, the treatment regimen includes pre-treatment with one agent, either the compound of the present invention or the anti-cancer agent, followed by the addition of the second agent for the duration of the treatment period.

In one particular embodiment of the present invention, the compound of the present invention can be administered in combination with any one or more of an additional compound of the present invention, an alkylating agent, an antibiotic agent, an antimetabolic agent, a hormonal agent, a plant-derived agent, an anti-angiogenic agent, a differentiation inducing agent, a cell growth arrest inducing agent, an apoptosis inducing agent, a cytotoxic agent, a biologic agent, a gene therapy agent, or any combination thereof.

The invention also includes methods of preventing the occurrence or progression of a cancer or a precancerous condition in a mammal comprising administering to the mammal an effective amount of a composition comprising a compound of the present invention and a pharmaceutically acceptable carrier.

The present invention also includes methods of treating or preventing cancer in a mammalian subject, comprising administering an effective amount to the mammalian subject a pharmaceutical preparation comprising a chemopreventive or chemotherapeutic compound of the present invention.

Cancer, as used herein includes, but is not limited to, malignant tumors, adenocarcinomas, carcinomas, sarcomas, malignant neoplasms, and leukemias. In particular epithelial cell derived cancers are intended to be encompassed by this invention. Examples of epithelial cell derived cancers that may be treated by the methods described herein include, but are not limited to, breast cancer, colon cancer, ovarian cancer, lung cancer or prostate cancer. Such cancers may be caused by, chromosomal abnormalities, degenerative growth and developmental disorders, mitogenic agents, ultraviolet radiating (UV), viral infections, oncogenes, mutations in genes, in-appropriate expression of a gene and presentation on a cell, or carcinogenic agent.

Administration of the compositions of the present invention may be for either a prophylactic or therapeutic use. When provided prophylactically, a compound of the present invention is provided in advance of any symptoms due to the cancer afflicting the individual. Additionally, a compound of the present invention may be administered during or after cancer treatment to help prevent the reoccurrence of cancer. The prophylactic administration of the composition is intended as a chemopreventive therapy and serves to either prevent initiation of malignant cells or arrest or reverse the progression of transformed premalignant cells to malignant disease.

When provided therapeutically the composition is provided at or after the onset of the disease. The therapeutic administration of the composition of this invention serves to attenuate or alleviate the cancer or facilitate regression of the cancer afflicting the individual. The term individual is intended to include any animal, preferably a mammal, and most preferably a human. Veterinary uses are intended to be encompassed by this definition.

In one embodiment of this invention, individuals at high risk for a particular cancer, or at high risk of reoccurrence of a cancer or who have known risk factors are prophylactically treated with the methods and compositions described herein. By way of example, such individuals may include those with a familial history for either early or late onset of cancer, and individuals who are being or have been treated for a cancer or cancer-related illness.

General ranges of suitable effective prophylactic dosages that may be used are about 0.1 mg/kg of body weight per day to about 500 mg/kg/day, a further range is about 0.5 mg/kg/day to about 250 mg/kg/day, and as a further range, about 1 mg/kg/day to about 100 mg/kg/day.

The daily dose of the compound may be administered in a single dose or in portions at various hours of the day. Initially, a higher dosage may be required and may be reduced over time when the optimal initial response is obtained. By way of example, treatment may be continuous for days, weeks, or years, or may be at intervals with intervening rest periods. The dosage may be modified in accordance with other treatments the individual may be receiving. One of skill in the art will appreciate that individualization of dosage may be required to achieve the maximum effect for a given individual. It is further understood by one skilled in the art that the dosage administered to a individual being treated may vary depending on the individuals age, severity or stage of the disease and response to the course of treatment. One skilled in the art will know the clinical parameters to evaluate to determine proper dosage for the individual being treated by the methods described herein.

Additional pharmaceutical methods may be employed to control the duration of action. Controlled release preparations may be achieved through the use of polymer to complex or absorb the proteins or their derivatives. The controlled delivery may be exercised by selecting appropriate macromolecules (for example polyester, polyamino acids, polyvinyl, pyrrolidone, ethylenevinylacetate, methylcellulose, carboxymethylcellulose, or protamine sulfate) and the concentration of macromolecules as well as the methods of incorporation in order to control release. Alternatively, instead of incorporating these agents into polymeric particles, it is possible to entrap these materials in microcapsules prepared, for example, by coacervation techniques or by interfacial polymerization.

When oral preparations are desired, the component may be combined with typical carriers/excipients, such as lactose, sucrose, starch, talc magnesium stearate, crystalline cellulose, methyl cellulose, carboxymethyl cellulose, glycerin, sodium alginate or gum arabic among others. The only limitation with resect to the carrier is that it does not deleteriously react with the active compound or is not deleterious to the recipient thereof.

The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with the active compounds.

As stated above, the administration of the compositions or of each individual component of the present invention may be for either a prophylactic or therapeutic purpose. The methods and compositions used herein may be used alone in prophylactic or therapeutic uses or in conjunction with additional therapies known to those skilled in the art in the prevention or treatment of cancer. Alternatively the methods and compositions described herein may be used as adjunct therapy.

It will be appreciated that the actual preferred amounts of active compounds used in a given therapy will vary according to the specific compound being utilized, the particular compositions formulated, the mode of application, the particular site of administration, etc. Optimal administration rates for a given protocol of administration can be readily ascertained by those skilled in the art using conventional dosage determination tests.

The present invention also comprises methods of treating cancer comprising administering an anti-cancer agent, anti-cancer chemotherapy and/or anti-cancer radiation treatment; and administering a treatment enhancing amount of a compound of the present invention.

Yet another method of the present invention is a method for treating a malignancy in a mammal, comprising administering a pharmaceutical compound or composition of the present invention with a therapy selected from the group consisting of radioimmunoconjugate administration, other forms of radiopharmaceutical therapy, chemotherapy, external beam therapy, surgery, and other anti-malignancy treatment.

Finally, another method of the present invention is a method of treating cancer comprising (a) administering to a patient in need of such treatment, a pharmaceutically-effective amount of a composition of the present invention and (b) administering a therapy selected from radiation therapy and chemotherapy.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Table 1: Table 1 shows the efficiency of various compounds synthesized in the present investigation as radiation sensitizers. The values were given as fraction of the cells survived when compared to DMSO control. Compounds 3, 4, and 15 were tested at 10 μM concentration. All other drugs were tested at 25 μM concentration.

TABLE 1

| Treatment | Survival Fraction |
|---|---|
| DMSO | 1.00 |
| DMSO + 6 Gy | 0.34 |
| 3 | 0.94 |
| 3 + 6 Gy | 0.43 |
| 4 | 0.93 |
| 4 + 6 Gy | 0.14 |
| 5 | 0.96 |
| 5 + 4 Gy | 0.45 |
| 6 | 0.87 |
| 6 + 6 Gy | 0.51 |
| 11 | 0.84 |
| 11 + 6 Gy | 0.29 |
| 12 | 0.99 |
| 12 + 6 Gy | 0.40 |
| 13 | 1.07 |
| 13 + 6 Gy | 0.33 |
| 14 | 0.8 |
| 14 + 6 Gy | 0.38 |
| 15 | 0.73 |
| 15 + 6 Gy | 0.32 |
| 16 | 0.94 |
| 16 + 6 Gy | 0.38 |
| 17 | 0.91 |
| 17 + 6 Gy | 0.33 |
| 18 | 0.99 |
| 18 + 6 Gy | 0.47 |
| 19 | 0.96 |
| 19 + 6 Gy | 0.35 |

Example 1

4-((3-((2,4,6-trioxotetrahydropyrimidin-5(6H)-ylidene)methyl)-1H-indol-1-yl)meth-yl)benzonitrile (1)

A mixture of barbituric acid (1.28 g; 0.01 mol) and 4-((3-formyl-1H-indol-1-yl)methyl)benzonitrile (2.60 g; 0.01 mol) in methanol (50 ml) were stirred at room temperature. After 10 min the reaction mixture became a solid suspension and the color of reaction mixture changed to yellow color solid suspension. The suspension continued to stir at room temperature for 5 hrs. Solid product was separated by filtration and washed several times with cold methanol (3×5 ml). The isolated yellow solid recrystallized from methanol gave (1) as a yellow crystalline product; m.p. >300° C.; $^1$H NMR (DMSO-$d_6$): δ 5.81 (s, 2H), 7.33-7.36 (m, 2H), 7.43-7.45 (d, 2H), 7.61-7.64 (m, 1H), 7.82-7.84 (d, 2H), 7.90-7.93 (m, 1H), 8.68 (s, 1H), 9.63 (s, 1H), 11.07 (bs, 1H), 11.15 (bs, 1H); $^{13}$C NMR (DMSO-$d_6$): δ 49.7, 109.4, 110.5, 110.8, 111.8, 117.9, 118.4, 123.0, 123.8, 128.0, 129.6, 132.6, 136.1, 141.7, 141.8, 142.6, 159.2, 162.9, 164.1.

Example 2

Methyl-4-((3-((2,4,6-trioxotetrahydropyrimidin-5(6H)-ylidene)methyl)-1H-indol-1yl)methyl)benzoate (2)

A mixture of barbituric acid (1.28 g; 0.01 mol) and methyl 4-((3-formyl-1H-indol-1-yl)methyl)benzoate (2.93 g; 0.01 mol) in methanol (50 ml) were stirred at room temperature. After 10 min the reaction mixture became a solid suspension and the color of reaction mixture changed to yellow color solid suspension. The suspension continued to stir at room temperature for 5 hrs. Solid product was separated by filtration and washed several times with cold methanol (3×5 ml). The isolated yellow solid recrystallized from methanol gave (2) as a yellow crystalline product; m.p. >300° C.; $^1$H NMR (DMSO-d$_6$): δ 3.82 (s, 3H), 5.79 (s, 2H), 7.33-7.36 (m, 2H), 7.40-7.42 (d, 2H), 7.61-7.63 (m, 1H), 7.91-7.93 (m, 1H), 7.94-7.95 (d, 2H), 8.68 (s, 1H), 9.62 (s, 1H), 11.06 (bs, 1H), 11.14 (bs, 1H); $^{13}$C NMR (DMSO-d$_6$): δ 49.9, 52.1, 109.2, 110.7, 111.8, 117.8, 122.9, 123.7, 127.4, 129.0, 129.5, 129.6, 136.2, 141.4, 141.7, 142.6, 150.1, 162.8, 164.1, 165.5.

Example 3

(Z)-4-((3-((2,5-dioxoimidazolidin-4-ylidene)methyl)-1H-indol-1-yl)methyl)benzo nitrile (7)

A mixture of hydantoin (1.00 g; 0.01 mol), 4-((3-formyl-1H-indol-1-yl)methyl)benzonitrile (2.60 g; 0.01 mol) and ammonium acetate (0.77 g; 0.01 mol) in acetic acid (2.70 g; 0.045 mol) were refluxed for 10 hrs. The reaction mixture was cooled and water (20 ml) was added. Filtered the product and washed with cold water (2×5 ml). The crude product was recrystallized from a mixture of methanol and ethyl acetate (1:1 v/v) gave (3) as a yellow crystalline product; m.p. >300° C.; $^1$H NMR (DMSO-d$_6$): δ 5.56 (s, 2H), 6.73 (s, 1H), 7.13-7.23 (m, 2H), 7.44-7.46 (d, 2H), 7.51-7.53 (d, 1H), 7.56 (m, 3H), 8.30 (s, 1H), 10.15 (bs, 1H), 11.07 (bs, 1H); $^{13}$C NMR (DMSO-d$_6$): δ 49.8, 100.4, 118.2, 110.4, 111.8, 118.2, 120.4, 122.5, 124.2, 126.8, 128.4, 129.9, 130.2, 134.8, 142.6, 142.6, 154.8, 164.8.

Experimental Protocols

Plating Efficiency (PE)

Figure 4:
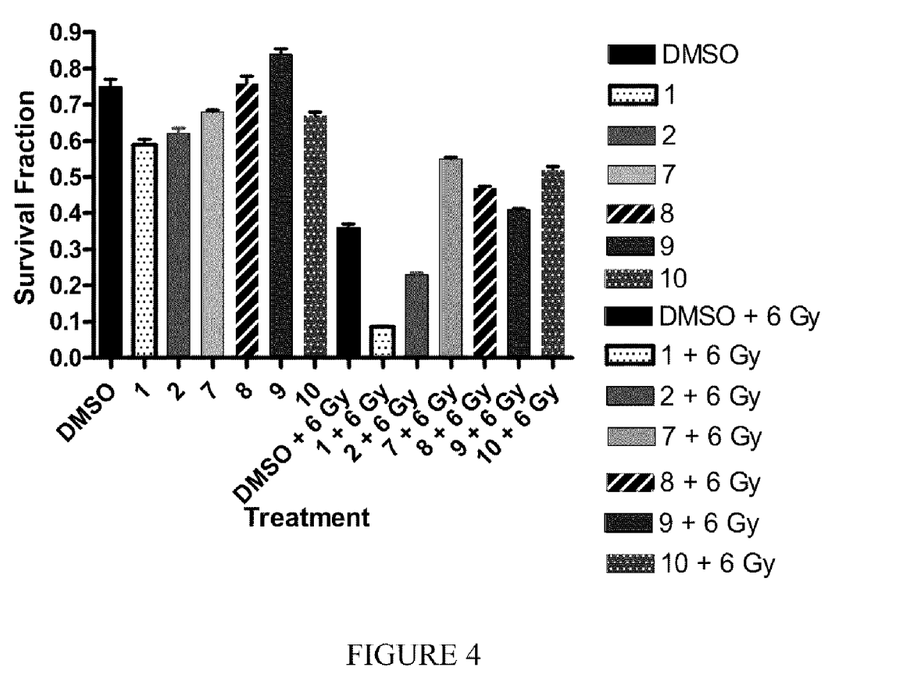
FIG. 4 shows the efficiency of various drugs that were synthesized (compounds 1, 2, 7, 8, 9, and 10) in the present investigation were analyzed for radiation sensitization.
Figure 5:
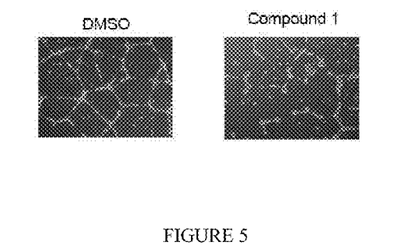
FIG. 5: HUVECs were plated on Matrigel, then treated wither DMSO or Compound 1 for 24 hrs. Tubule formation was assessed by looking under microscope. Compound 1 inhibited tubule formation.

Human colon carcinoma cells (HT-29) were grown in DMEM/F-12 medium containing 10% fetal bovine serum (FBS). The cells were inoculated into T25 flasks (200-600 cells per flask). All compounds/drugs were dissolved in DMSO. Cells were treated either with carrier (DMSO) or drugs at 10-150 μM concentration. The flasks were incubated at 37° C. for 30 mins. After 30 mins incubation, the cells were radiated using Cs source. The flasks were then incubated at 37° C. for 90 mins. The medium was removed and washed with PBS. Fresh medium was added to the flasks and incubated at 37° C. for several days (2-3 weeks) to form colonies. The cells were fixed with methanol-acetic acid (3:1 ratio) and stained with 1% crystal violet dye in methanol for 30 min. The excess dye was washed away with de-ionized water, and the colonies were counted. The plating efficiency was determined by comparing the number of colonies obtained from treated flasks with those obtained from control flasks. Bar graphs were created using the above data (FIG. 4).

HSP70 Expression Experiment

Figure 1:
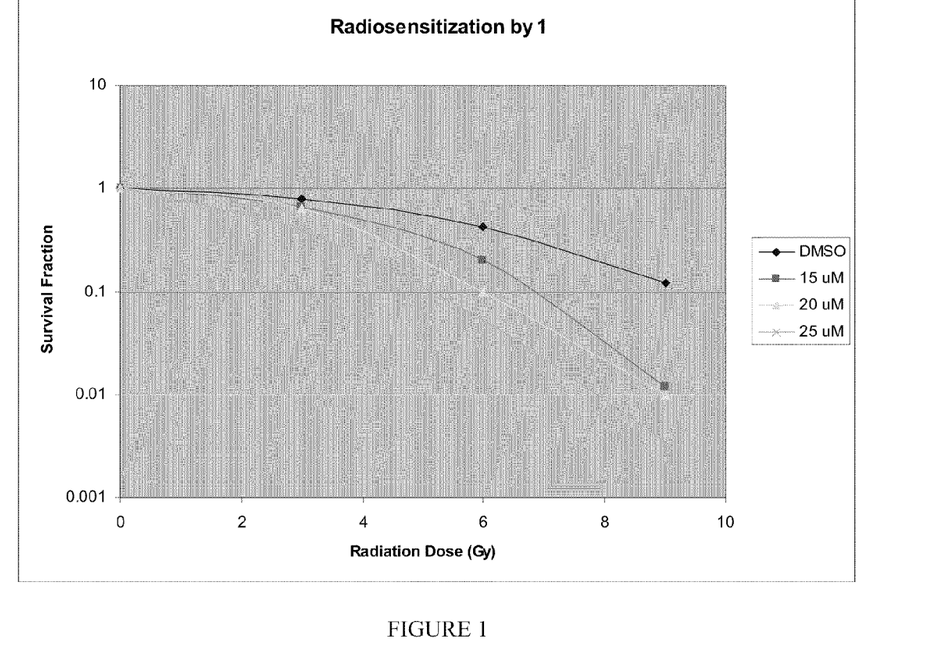
Figure 2:
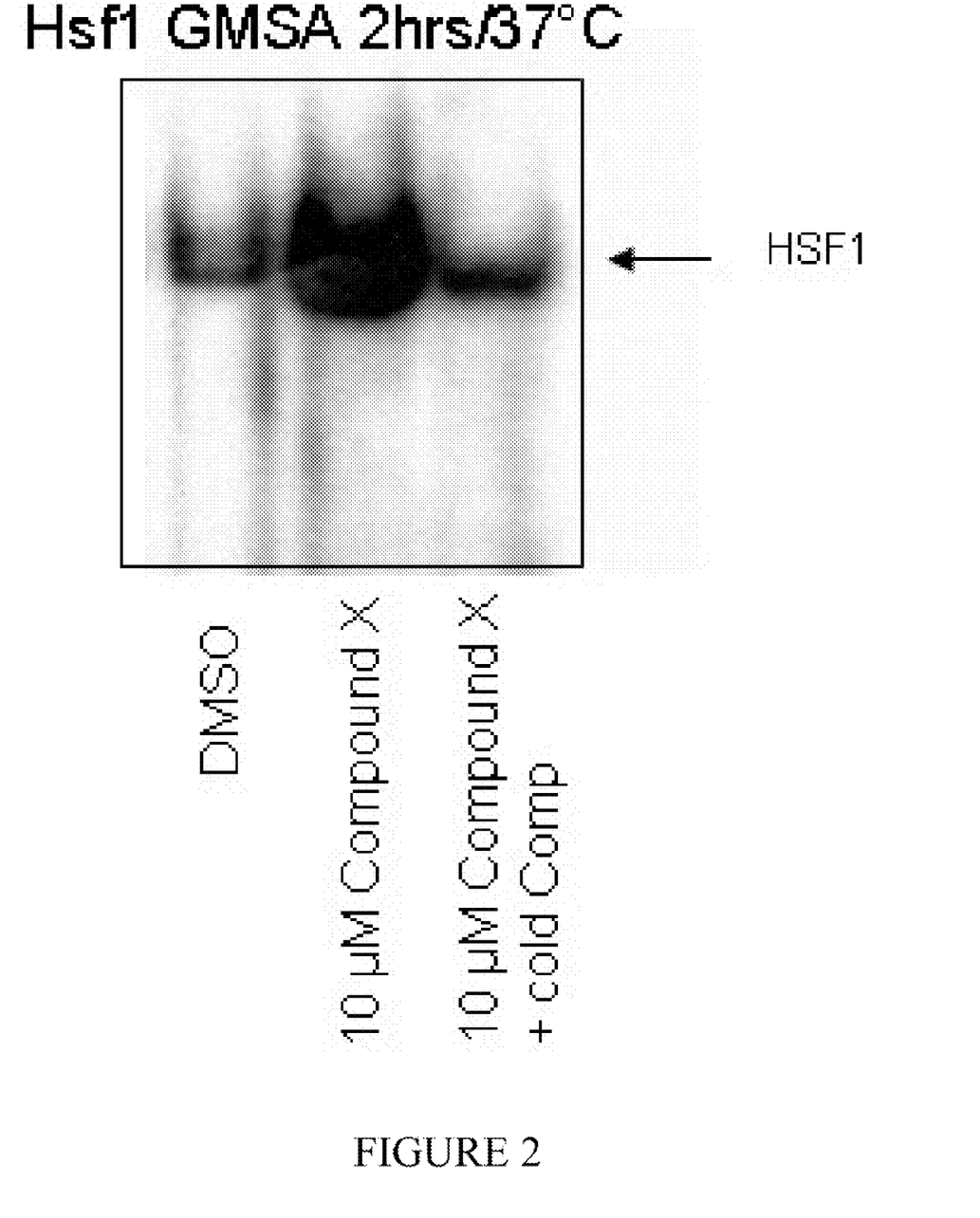
Figure 3:
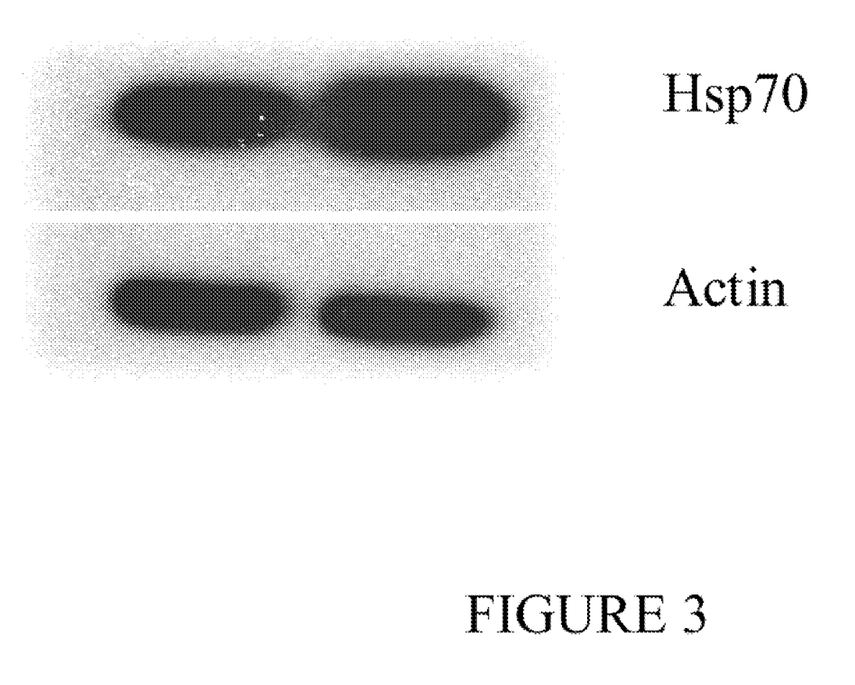
FIG. 3: Nuclear extracts obtained above were used to detect the expression of HSP70 protein by Western Blot. Actin was used as loading control.

HT-29 cells were plated and were allowed to grow to 75% confluency. The cells were treated either with DMSO or drugs for 2 hrs. Cells were washed with phosphate buffered saline (PBS, pH 7.2), fresh medium was added, and incubated at 37° C. for 5 hrs. Then the cells were washed 3 times with cold PBS. Then, 150 μl of protein lysis buffer (50 mM Tris HCl, pH 7.5, 150 mM NaCl, 1% NP-40, 10 mM EDTA, 0.1% SDS, 0.5% deoxycholic acid and 10 μl/ml of protein inhibitor cocktail (Sigma, cat #E8230) was added and the cells were scraped. The lysate was transferred to a fresh Eppendorf tube (1.5 ml) and sonicated for 5 seconds. The lysate was centrifuged at 13000 rpm at 4° C. for 20 min. The supernatant was transferred to fresh tubes and protein was measured from each sample using a Biorad colorimetric assay. 20-40 μg of protein was taken in a fresh tube and was added equal volume of 5× Lemmeli buffer and the samples were heated at 95° C. for 5 min. The samples were cooled and centrifuged briefly. The samples were loaded on polyacrylamide gels (10-12%) and resolved by gel electrophoresis. Then the proteins were transferred onto a nitrocellulose membrane and the membrane was blocked with 5% low fat milk in TBS-T buffer (contains 0.2% Tween-20). HSP70 antibodies were diluted 2000 fold in 5% milk in TBS-T and added to the membrane and shaken for 3-4 hrs. Membranes were washed 3 times with 1-5% milk in TBS-T. HRP conjugated secondary antibodies were diluted 2000 fold in 1-5% milk in TBS-T and incubated the membrane for 45 min with shaking. The membrane was washed 3 times with TBS-T for 10 min. each time. 10 ml of ECL reagent (Amersham) was added to the membrane for 1 min. The membrane was exposed to autoradiography film and developed (FIG. 3)

Gel Mobility Shift Assay

HT-29 cells were incubated at 37° C. for 2 hrs. in the presence of various concentrations of drugs. After the treatment, cells were washed with PBS and fresh medium was added. The flasks were incubated another 5 hrs at 37° C. Gel mobility shift assay was done as described in Kim et al. (2006). Briefly, the nuclear protein was extracted with buffer containing 10 mM HEPES, 422 mM NaCl, 0.1 mM EGTA, 5.3% glycerol, and protease inhibitor cocktail. Binding reactions were performed by adding 10-20 μg of cell extract to 0.2 ng of 32P-labeled, double-stranded oligonucleotide containing rat Hsp70 heat shock element (Liu et al., 1993) in binding buffer [20 mM Tris (pH 7.5), 100 mM NaCl, 1 mM DTT, 10% glycerol, 0.05% NP-40, 5 mM MgCl2, 0.05 μg of poly dI-dC] and incubating at 20° C. for 15 min. Competition binding reactions were performed by addition of a 100-fold excess of unlabeled HSE to the binding reaction.

Tubule Formation Assay

Figure 6:
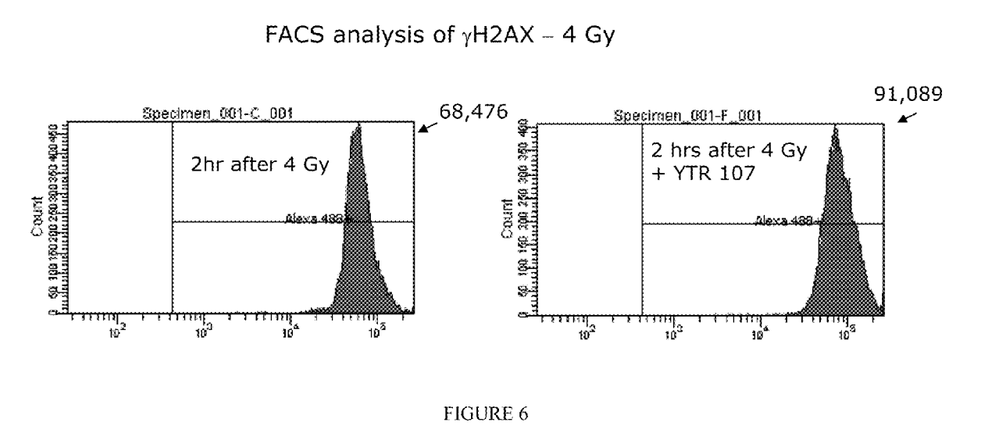
FIG. 6 shows YTR increases radiation-induced phosphorylation of H2AX, a biochemical measure of DNA double strand breaks
Figure 7:
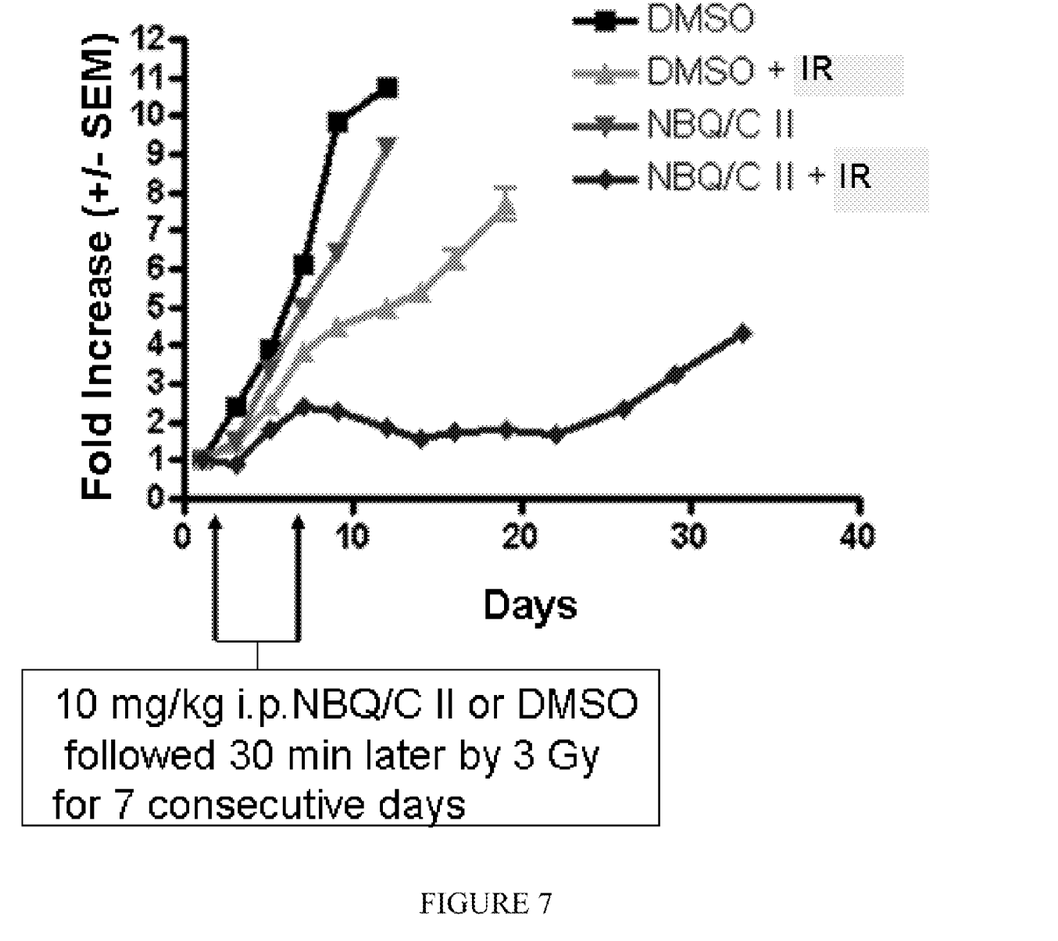
FIG. 7 shows inhibition of tumor growth in connection with the present invention.

Human umbilical vascular endothelial cells (HUVECs) (50,000 cells/well) were plated on Matrigel. After 30 min, the cells were treated either with DMSO or 25 μM Compound 1. Tubule formation was assessed by observing plates under microscope. FIG. 6 is represents 24 hr time point for DMSO and Compound 1.

As indicated above, throughout this application, various references are mentioned. All references, specifically those listed below, are incorporated herein by reference in their entirety and should be considered to be part of this application.

REFERENCES

Bradbury, C. M., Markovina, S., Wei, S. J., Rene, L. M., Zoberi, I., Horikoshi, N. and Gius, D. (2001) Indomethacin-induced radiosensitization and inhibition of ionizing radiation-induced NF-KB activation in HeLa cells occur via a mechanism involving p 38 MAP kinase. *Cancer Res*, 61, 7689-7696.

Kampinga, H. H. and Dikomey, E. (2001) Hyperthermic radiosensitization: mode of action and clinical relevance. *Int J Radiat Biol*, 77, 399-408.

Kim K W, Mutter R W, Cao C, Albert J M, Shinohara E T, Sekhar K R, Lu B. (2006) Inhibition of signal transducer and activator of transcription 3 activity results in downregulation of Survivin following irradiation. *Mol Cancer Ther.* 5:2659-65.

Locke, J. E., Bradbury, C. M., Wei, S. J., Shah, S., Rene, L. M., Clemens, R. A., Roti Roti, J., Horikoshi, N. and Gius, D. (2002) Indomethacin lowers the threshold thermal exposure for hyperthermic radiosensitization and heat-shock inhibition of ionizing radiation-induced activation of NF-kB. *Int J Radiat Biol*, 78, 493-502

Nielsen, O. S., Horsman, M. and Overgaard, J. (2002) A future for hyperthermia in cancer treatment? *Eur J Cancer*, 37, 1587-1589.

Raaphorst, G. P. and Azzam, E. I. (1983) Thermal radiosensitization in Chinese hamster (V79) and mouse C3H 10T ½ cells. The thermotolerance effect. *Br J Cancer*, 48, 45-54.

Sekhar K R, Sonar V N, Muthusamy V, Sasi S, Laszlo A, Sawani J, Horikoshi N, Higashikubo R, Bristow R G, Borrelli M J, Crooks P A, Lepock J R, Roti Roti J L, Freeman M L. (2007). Novel chemical enhancers of heat shock increase thermal radiosensitization through a mitotic catastrophe pathway. *Cancer Res*, 67: 695-701.

Sonar V N, Thirupathi Reddy Y, Sekhar K R, Sasi S, Freeman M L, Crooks P A. (2007) Novel substituted (Z)-2-(N-benzylindol-3-ylmethylene)quinuclidin-3-one and (Z)-(+/−)-2-(N-benzylindol-3-ylmethylene)quinuclidin-3-ol derivatives as potent thermal sensitizing agents. *Bioorg Med Chem. Lett.* 17:6821-4.

Xu, M., Myerson, R. J., Straube, W. L., Moros, E. G., Lagroye, I., Wang, L. L., Lee, J. T. and Roti Roti, J. L. (2002) Radiosensitization of heat resistant human tumor cells by 1 hour at 41.1° C. and its effect on DNA repair. *Int J Hyperthermia*, 18, 385-403.

Wynstra, J. H., Wright, W. D., Higashikubo, R. and Roti Roti J. L. (1990) Repair of radiation-induced DNA damage in thermotolerant and nonthermotolerant HeLa cells. *Radiat Res*, 124, 85-89.

Zhouguang, H., Yexiong, L., Weizhi, Y., Junxin, W. and Zihao, Y. (2003) Abrogation of radiation-induced G2 arrest and radiosensitization by 7-hydroxystaurosporine (UCN-01) in human nasopharyngeal carcinoma cell line. *Aizheng*, 22, 6-10.

The invention thus being described, it would be obvious that various changes in the details, steps and materials that have been described herein may be made by those skilled in the art within the principles and scope of the invention herein illustrated and defined in the appended claims. Therefore, while the present invention has been shown and described herein in what is believed to be the most practical and preferred embodiment, it is recognized that departures can be made therefrom within the scope of the invention, which is therefore not to be limited to the details disclosed herein but is to be accorded the full scope of the claims so as to embrace any and all equivalent apparatus and methods.

We claim:

1. A compound of the following formula:

wherein (a) $R_2$ is H and $R_7$ is CN; or
(b) $R_2$ is H and $R_7$ is COOCH$_3$; or
(c) $R_2$ is H and $R_7$ is H; or
(d) $R_2$ is H and $R_7$ is NO$_2$; or
(e) $R_2$ is C$_1$ and $R_7$ is H; or
(f) $R_2$ is OCH$_3$ and $R_7$ is H; and pharmaceutical compositions thereof.

2. A compound of the following formula:

wherein (a) $R_2$ is H, $R_5$ is H, and $R_7$ is CN; or
(b) $R_2$ is H, $R_5$ is H, and $R_7$ is CN; or
(c) $R_2$ is H, $R_5$ is H, and $R_7$ is NO$_2$; or
(d) $R_2$ is H, $R_5$ is H, and $R_7$ is Cl; or
(e) $R_2$ is H, $R_5$ is H, and $R_7$ is COOCH$_3$; or
(f) $R_2$ is H, $R_5$ is Br, and $R_7$ is CN; or
(g) $R_2$ is H, $R_5$ is H, and $R_7$ is F; or
(h) $R_2$ is C$_1$, $R_5$ is H, and $R_7$ is CN; or
(i) $R_2$ is Br, $R_5$ is H, and $R_7$ is OCH$_3$; or
(j) $R_2$ is CH$_3$, $R_5$ is H, and $R_7$ is H; or
(k) $R_2$ is Br, $R_5$ is H, and $R_7$ is H; or
(l) $R_2$ is OCH$_3$, $R_5$ is H, and $R_7$ is H; or
(m) $R_2$ is H, $R_5$ is H, and $R_7$ is CH$_3$; and pharmaceutical compositions thereof.

3. A compound of claim 1, of the following formula:

4. A compound of claim 1, of the following formula:

5. A compound of claim 2, of the following formula:

6. A compound of claim 1, of the following formula:

7. A compound of the following formula:

wherein

X is O or N; R is H, methyl, phenyl or substituted phenyl; $R_1$-$R_{11}$ are each independently selected from H, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, arylalkenyl, substituted arylalkenyl, arylalkynyl, substituted arylalkynyl, arylalkenyl, substituted arylalkenyl, arylalkynyl, substituted arylalkynyl, heteroaryl, substituted heteroaryl, trifluoromethyl, halogen, cyano, nitro, amidinea, amino, carboxyl, ester, alkylalkylamino, dialkylamino, hydroxyl, alkoxy or arylalkoxy; and pharmaceutical compositions thereof.

8. A compound of the following formula:

X is O or N; R is H, methyl, phenyl or substituted phenyl; $R_1$-$R_{11}$ are each independently selected from H, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, arylalkenyl, substituted arylalkenyl, arylalkynyl, substituted arylalkynyl, arylalkenyl, substituted arylalkenyl, arylalkynyl, substituted arylalkynyl, heteroaryl, substituted heteroaryl, trifluoromethyl, halogen, cyano, nitro, amidinea, amino, carboxyl, ester, alkylalkylamino, dialkylamino, hydroxyl, alkoxy or arylalkoxy; and pharmaceutical compositions thereof.

9. A pharmaceutical composition comprising a compound of formula 11, and a pharmaceutically acceptable carrier.

10. A pharmaceutical composition comprising a compound of formula 12, and a pharmaceutically acceptable carrier.

11. A pharmaceutical composition comprising a compound of formula 17, and a pharmaceutically acceptable carrier.

12. A pharmaceutical composition comprising a compound of formula 18, and a pharmaceutically acceptable carrier.

13. A pharmaceutical composition comprising a compound of formula 11, and a pharmaceutically acceptable carrier.

14. A pharmaceutical composition comprising a compound of formula 11, and a pharmaceutically acceptable carrier.

* * * * *